(12) United States Patent
Poortinga

(10) Patent No.: US 9,814,676 B2
(45) Date of Patent: Nov. 14, 2017

(54) ENCAPSULATION SYSTEM

(71) Applicant: Bether Encapsulates B.V., Groningen (NL)

(72) Inventor: Albert Thijs Poortinga, Apeldoorn (NL)

(73) Assignee: Bether Encapsulates B.V. (NL)

( * ) Notice: Subject to any disclaimer, the term of this patent is extended or adjusted under 35 U.S.C. 154(b) by 0 days.

(21) Appl. No.: 14/421,174

(22) PCT Filed: Aug. 19, 2013

(86) PCT No.: PCT/NL2013/050603
§ 371 (c)(1),
(2) Date: Feb. 12, 2015

(87) PCT Pub. No.: WO2014/030995
PCT Pub. Date: Feb. 27, 2014

(65) Prior Publication Data
US 2015/0202151 A1    Jul. 23, 2015

(30) Foreign Application Priority Data

Aug. 20, 2012   (NL) .................................... 2009335

(51) Int. Cl.
| | | |
|---|---|---|
| *A61K 9/113* | (2006.01) | |
| *A23L 1/00* | (2006.01) | |
| *A61K 9/19* | (2006.01) | |
| *B01J 13/14* | (2006.01) | |
| *C09B 67/02* | (2006.01) | |
| *A23P 10/30* | (2016.01) | |
| *A61K 9/50* | (2006.01) | |

(52) U.S. Cl.
CPC .............. *A61K 9/113* (2013.01); *A23P 10/30* (2016.08); *A61K 9/19* (2013.01); *B01J 13/14* (2013.01); *C09B 67/0097* (2013.01); *A23V 2002/00* (2013.01); *A61K 9/5073* (2013.01)

(58) Field of Classification Search
CPC ........... A23L 1/0029; A23P 1/04; B01J 13/14; A61K 9/19; A61K 9/5073; A61K 9/113; A23V 2002/00; C09B 67/0097
See application file for complete search history.

(56) References Cited

U.S. PATENT DOCUMENTS

2012/0121516 A1    5/2012   Tabeling et al.

FOREIGN PATENT DOCUMENTS

WO    2011053803    5/2011

OTHER PUBLICATIONS

Binks, B., et al., "Solid Wettability from Surface Energy Components: Relevance to Pickering Emulsions," Langmuir 2002, 18, 1270-1273.
Dorbolo, S., et al., "Antibubble lifetime: Influence of the bulk viscosity and of the surface modulus of the mixture," Physicochem. Eng. Aspects 365 (2010) 43-45.
Dorbolo, S., et al., "Vita brevis of antibubbles," Europhysicsnews, 2006, 24, vol. 37, No. 4, 24-25.
Golemanov, K., et al., "Latex-Particle-Stabilized Emulsions of Anti-Bancroft Type," Langmuir 2006, 22, 4968-4977.
Gouin, S., et al., "Micro-encapsulation: industrial appraisal of existing technologies and trends," Trends in Food Science & Technology 15 (2004) 330-347.
Lentacker, I., et al., "Drug loaded microbubble design for ultrasound triggered delivery," Soft Matter, 2009, 5, 2161-2171.
Poortinga, A., "Long-Lived Antibubbles: Stable Antibubbles through Pickering Stabilization," Langmuir 2011, 27, 2138-2141.
Postema, M., et al., "Generation of a Droplet Inside a Microbubble with the Aid of an Ultrasound Contrast Agent: First Result," Letters in Drug Design & Discovery, 2007, 4, 74-77.
Bernard P. Binks and Ryo Murakami "Phase inversion of particle-stabilized materials from foams to dry water" published online: Oct. 15, 2006. Nature materials, London Nature Publishing, vol. 5, Group Pag-ISSN/ISBN: 1476-4660.
Prasad S. Bhosale and Mahesh V. Panchagnula "Sweating Liquid Micro-Marbles: Dropwise Condensation on Hydrophobic Nanoparticulate Materials" Langmuir 2012, 28, 14860-14866.
"Terminal velocity" Wikipedia, Jan. 24, 2014.
Laurent Forny, et al. "Storing water in powder form by self-assembling hydrophobic silica nanoparticles" Powder Technology 2007, 171, 15-24.
G. McHale and M.I. Newton "Liquid marbles: topical context within soft matter and recent progress" Soft Matter, 2015, 11, 2530-2546.
Jeffrey M. Aristoff and John W. Bush, Water entry of small hydrophobic spheres, J. Fluid Mech. 619:45-78 (Jan. 25, 2009).
Wendy Duncan-Hewitt and Rozalia Nisman, Investigation of the surface free energy of pharmaceutical materials from contact angle, sedimentation, and adhesion measurements, J. Adhesion Sci. & Tech. 7(3):263-283 (1993).

*Primary Examiner* — Johann R Richter
*Assistant Examiner* — Genevieve S Alley
(74) *Attorney, Agent, or Firm* — Patterson Intellectual Property Law PC; Seth R. Ogden; Emily A. Shouse

(57) ABSTRACT

The invention pertains to an encapsulation system; in particular a 3-phase system comprising an inner, second and outer phase wherein the second phase is gaseous, and wherein the 3-phase system has a lifetime of at least 3 min and the second phase has a diameter of less than 1 mm. An example of such a system is a stable, small antibubble. Also, the invention pertains to methods of making such 3-phase systems, and to use and methods of use thereof. In particular, 3-phase systems according to the invention are stabilized by surface active particles or molecules, such as for instance colloidal particles. The 3-phase systems of the invention can include a variety of other compounds, and can among others be used in pharmaceutical- or food-based applications. In particular, a 3-phase system according to the invention, such as for example an antibubble, may deliver pharmaceutical compounds.

9 Claims, 5 Drawing Sheets ref. 3.2

US 9,814,676 B2

ENCAPSULATION SYSTEM

BACKGROUND OF THE INVENTION

Cross-Reference to Related Applications

This application is the National Stage of International Application No. PCT/NL2013/050603, filed Aug. 19, 2013 which claims priority to Netherlands Application No. 2009335, filed Aug. 20, 2012.

TECHNICAL FIELD

The invention is in the field of encapsulation systems, preferably stable multiphase encapsulation systems.

BACKGROUND ART

Encapsulation is an important technological field and numerous encapsulates have already been developed (see e.g. S. Gouin, Trends in food science and technology 15 (2004) 330-347 for an overview). A major challenge in encapsulation has been to produce encapsulates that on the one hand are able to encapsulate a substance without leakage and on the other hand can be triggered to release their contents completely and in a short period of time. An example of a class of encapsulates designed to achieve this are microbubbles.

The use of microbubbles for the triggered release of drugs is gaining more and more interest. Microbubbles are bubbles in a size range of microns to millimetres, and typically consist of a gaseous phase inside a liquid or solid phase. The boundary shell can be stabilized by a solid. Microbubbles can be loaded with various compounds, such as for instance pharmaceutically active compounds. This is achieved by incorporating these compounds on the outside or the inside of the boundary shell of the microbubble, potentially by aid of an oil layer adhered to the boundary shell. Thus such microbubbles consist of an inner gaseous phase with optionally a solid or solid/liquid boundary, dispersed in an outer, liquid or solid phase. An overview of methods to load microbubbles with compounds, such as for instance drugs, is given in FIG. 1 (taken from I. Lentacker, S. C. De Smedt, N. N. Sanders, Drug loaded microbubble design for ultrasound triggered delivery, Soft Matter, 2009, 5, 2161-2170). Typically the microbubbles are triggered to release the compounds using ultrasound.

Several drawbacks of such loaded microbubbles have been identified though. First, the amount of active compound that can be loaded is generally low. Second, release is generally incomplete, too slow or takes place only when high levels of ultrasound are applied, which may lead to side effects when release needs to take place in a mammal.

Antibubbles have been proposed to solve these issues (see U.S. Patent 2002/0159952 or M. Postema et al, Letters in Drug Design & Discovery, 2007, 4, 74-77). Antibubbles typically have at least three phases, wherein a liquid phase is comprised in a gaseous phase that is in turn dispersed in a liquid phase. However, although antibubbles have been observed, they can not be obtained with a sufficiently long lifetime to render them industrially useful. The lifetime of antibubbles is short, typically in the order of minutes (see S. Dorbolo et al, Vita brevis of antibubbles, Europhys. News 2006, 37, 24-25). "Lifetime" is defined as the time until half of the antibubbles has lost their inner droplet(s). Also, useful antibubbles typically are small, and small antibubbles generally are less stable, i.e. have a shorter lifetime, than larger antibubbles S. Dorbolo et al. (Colloids and Surfaces A: Physicochem. Eng. Aspects 365 (2010) 43-45) recently described attempts to increase the stability of 10 mm antibubbles by increasing the viscosity of the liquid containing the antibubble, i.e. the continuous phase, and by increasing the interfacial elasticity of the antibubble interfaces. This led to an average antibubble lifetime in the order of only a few minutes. The limited stability of antibubbles has been explained by the fact that because of the low dielectric permittivity and the low solvent quality of the gas film, surfactants adsorbed at both interfaces hardly generate electrostatic or hydrophobic repulsive forces in-between both interfaces.

Antibubbles are not only rather unstable, antibubbles smaller than a millimetre, which is a size range that is very relevant for practical applications, have hardly ever been reported (see M. Postema et al, Letters in Drug Design & Discovery, 2007, 4, 74-77). According to the equation proposed by Dorbolo (Vita brevis of antibubbles, Europhys. News 2006, 37, 24-25) in which the lifetime of the antibubbles is proportional to their size, these small antibubbles have an even shorter lifetime in the order of seconds, which is far too short for practical applications.

Recently we showed for the first time that antibubbles with a lifetime of tens of hours can be produced by having colloidal particles adsorb at the fluid-gas interfaces of the antibubbles (A. T. Poortinga, Langmuir 27, 2138-2141 (2011). However, the method of making these antibubbles can only work for antibubbles with a size of at least one millimetre. The method used there does not allow scaling down to smaller sizes for two reasons. First, the method consists of contacting a droplet of water with a layer of hydrophobic colloidal particles in order to coat the droplet. Since the colloidal particles are present in air they cannot be dispersed and as a result the water droplet will be coated with aggregates of colloidal particles. In the mentioned report (Langmuir 27, 2138-211 (2011)) these aggregates of colloidal particles have a diameter in the order of 10 micron. Because the water droplet needs to be coated with a layer of these aggregates of colloidal particles, this method can never lead to antibubbles with a size in the order of tens of microns.

Second, the coated water droplets are, after gelling, dropped in an aqueous solution which leads to the coated droplets being captured in a bubble. In order for this to occur the kinetic energy of the coated droplet has to be high enough to overcome the interfacial tension forces of the water. One can calculate that if the coated water droplet has a size of 20 micron it would need to hit the water with a speed of a few m/s. However, Stokes law predicts that such a droplet will have a fall velocity in the order of cm/s only. Next to that, the method described in Langmuir 27, 2138-211 (2011) requires the core of the antibubbles to be gelled, which may be a drawback, for example since it will slow down release.

Thus a need still exists for antibubbles with a size smaller than a millimetre and a lifetime of at least 10 minutes. The present invention provides a method to achieve stable 3-phase system in which the middle, second phase is gaseous, and therefore provides among others such antibubbles.

SUMMARY OF THE INVENTION

The invention pertains to stable 3-phase systems, in which a second phase is dispersed in an outer phase, said second phase being gaseous. Said second phase further comprises at least one additional phase. The invention pertains to methods of making such 3-phase systems, and to uses thereof. In particular the invention comprises a method of producing a 3-phase system comprising an inner, second and outer phase, comprising making a 2-phase system comprising a dispersed and a continuous phase in which the continuous phase is a volatile compound, dispersing said 2-phase system in a third phase to obtain a ternary mixture, and removing or evaporating the volatile compound so that the second phase becomes gaseous.

Preferably in said method the 3-phase system is stabilized by surface active particles or molecules. In a further preferred embodiment the outer phase is aqueous. Further preferred is an embodiment wherein the volatile compound is a volatile organic liquid.

In an embodiment of the invention the stable 3-phase system has a lifetime of at least 3 minutes. Further preferred is a 3-phase system wherein the diameter of the second phase has a size smaller than 1 mm.

In a further aspect of the invention, the surface active particles or molecules that may be used comprise colloidal particles.

Further preferred is an embodiment wherein any aqueous phase additionally comprises a glass-forming material and preferably then both the inner and the outer phase are aqueous.

Also preferred is a method according to the invention wherein removing or evaporating the volatile compound is achieved by freeze-drying.

In a further embodiment of the method of the invention the outer phase is subsequently solidified, preferably by polymerization.

The invention further comprises a 3-phase system comprising at least an inner, second and outer phase wherein the second phase is gaseous, comprises at least an inner phase and is dispersed in the outer phase, said 3-phase system having a lifetime of at least 3 min and wherein said second phase has a diameter of less than 1 mm. Preferably such a system comprises surface active particles or molecules at least one of the interfaces between the phases. In a preferred embodiment, the invention comprises a 3-phase system wherein the outer phase is aqueous. Further preferred is a system wherein the outer phase comprises a water-soluble solid.

Also preferred is a 3-phase system wherein the inner phase is aqueous, and further preferred said inner phase comprises a water-soluble compound.

Further part of the invention is a 3-phase system according to the invention wherein the inner phase further comprises a solid.

Further preferred is a 3-phase system according to the invention wherein the inner phase comprises a pharmaceutical compound or food compound.

In another embodiment of the invention the inner and outer phases of the 3-phase system consist of acceptable food ingredients. In yet a further embodiment the inner phase comprises a solid.

In a further preferred embodiment the outer phase comprises an organic liquid, preferably a polymerisable organic liquid. In such a case, the invention also relates to a 3-phase system obtainable by polymerising the before defined 3-phase system 22.

The invention further relates to the use of a 3-phase system according to the invention as a pharmaceutical carrier. An alternative use may be the use of the system of the invention in a food product.

Further, the 3-phase system according to the invention is used to create sinking, floating or neutral buoyancy bubbles.

A preferred further use of the system according to the invention is the use as a foamed polymer.

Further, the invention relates to the use of a method according to the invention to prepare a stable 3-phase system of which the second phase is gaseous.

In yet another embodiment, the invention relates to a solid powder that upon reconstitution with a liquid provides an antibubble solution.

Yet another application of the 3-phase system of the invention is the use to encapsulate at least one compound.

DETAILED DESCRIPTION OF INVENTION

Figure 1:
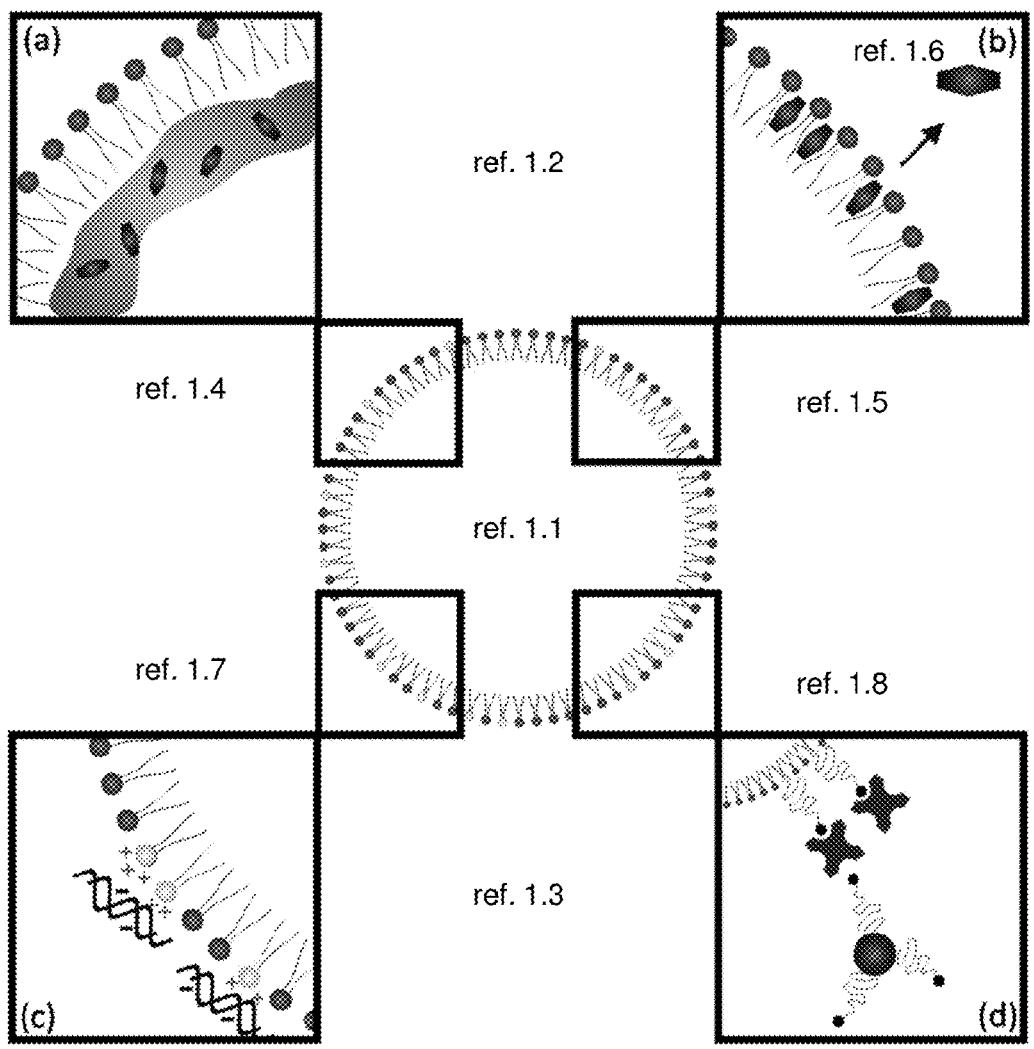
FIG. 1: Schematic overview of existing principles of controlled release using microbubbles.

A 3-phase system is a multiphase system in which at least three distinct phases can be observed, separated by at least two interfaces. For the context of the present invention, a 3-phase system is limited to a 3-phase system in which there exists one continuous "outer" phase. In said outer phase, a multiphase system of at least two phases is dispersed as one or more small entities. This multiphase system of at least two phases comprises an outer "second" phase, surrounding a therein distributed inner phase. A 3-phase system according to the present invention is characterized in that the outer "second" phase of the dispersed multiphase system of at least two phases is gaseous. However, the inner phase of the dispersed multiphase system of at least two phases may itself be a 2-phase system, such as a liquid in which there is a dispersion of solid particles. Such 3-phase systems may be used to encapsulate a compound such as a pharmaceutical, a flavour, a density-increasing solid, a peptide, a nucleotide, a mineral or any other compound or combination of compounds that requires encapsulation for a given purpose. The inner phase may even encapsulate biological material such as cells, micro-organisms, virus particles and the like.

Furthermore, the continuous outer phase of the 3-phase system may, in addition to the dispersed multiphase system of at least two phases, further may comprise another immiscible phase, such as dispersed particles or bubbles. For this reason, the invention is not limited to a 3-phase system, but may be any multiphase system in which 3 or more phases are present, and wherein at least one dispersed gaseous phase exists, which comprises one or more different phases.

A 3-phase system according to the invention is characterized in that the continuous outer phase comprises a dispersed multi-phase system of which the outer phase is air, and which dispersed multiphase system comprises at least one therein distributed phase.

Other systems comprising 3 phases are known in the art. An example is a system in which the outer phase is liquid, and in which the dispersed inner phase is a liquid, comprising a dispersed liquid phase. Such a system is customarily called a double emulsion. A double emulsion may be a water-oil-water ("wow") emulsion, having a continuous water phase, with therein distributed an organic phase that comprises a dispersed aqueous phase. Alternatively, such a system may be an oil-water-oil ("owo") emulsion, comprising a continuous organic phase, in which there is distributed an aqueous phase comprising a dispersed organic phase. However, such phases do not have as a second phase a gaseous phase, but instead have as second phase a liquid phase. This distinguishes 3-phase systems of the invention from double emulsions.

Furthermore, regular bubbles can be considered a 3-phase system of gas-liquid-gas. However, also in this case the second phase is not gaseous, and thus the present invention can not be considered a bubble The term "phase" is known in the art, and refers to a gaseous, liquid or solid molecularly homogeneous continuum. In a multiphase system, phases do not completely mix and thus display at least partly prohibited diffusion over the interface that separates two phases. In such a case phases are said to be immiscible.

Thus, a gaseous phase refers to a gas or gas mixture. A solid phase refers to a single solid, or a homogeneous mixture of different solids. Although a heterogeneous mixture of solids, or even a homogeneous solid powder, may be considered 2-, or even 3-phase systems (because of the air between powder particles), for practical reasons in the context of the present invention, a solid phase will be considered a single phase, because a solid phase does not mix with an adjacent phase and thus displays prohibited diffusion over the interface that separates the solid from its surrounding phase(s). If however a solid phase were to dissolve slowly in an adjacent liquid phase, or to sublime into an adjacent gaseous phase, this solid phase is a separate phase only until the solid phase is fully distributed in the adjacent phase. Of course, in such a case it cannot be said that such solid phase is stable.

A liquid phase is liquid, but may comprise various fully miscible liquids, or dissolved solids or gases, as long as said liquid phase does not comprise an interface over which there is prohibited diffusion of one or more of the liquid phase's constituents. As is customary in the art, a liquid phase may be an aqueous phase, which by definition is polar. Often, but not necessarily, one of the polar constituents is water. However, the polar constituent may also comprise water-miscible other liquids. Such liquids may be water-dissolvable organic liquids, as long as they are fully dissolved in the aqueous phase. An example is for instance an alcohol, such as ethanol, or a small organic acid, such as acetic acid. Also, an aqueous phase may comprise fully dissolved solids, such as for example salts, proteins or carbohydrate polymers.

A liquid phase may also be an organic phase. By definition, an organic phase is less polar than an aqueous phase, and does not fully mix with an aqueous phase. Therefore, any mixture of an organic and an aqueous phase will display an interface layer over which there exists prohibited diffusion, and will be denominated as "biphasic". An organic phase may further comprise one or more fully miscible liquids or gases, and may also comprise small amounts of water, as long as these are fully dissolved so as to be comprised in the single organic phase. It may further comprise one or more fully dissolved solids, such as for instance organic solids.

An embodiment of a 3-phase system according to the invention is an antibubble. An antibubble is a 3-phase system in which the second phase is gaseous, and in which the inner and outer phase are both liquid. Optionally, the inner and/or the outer phase further comprise a dispersed solid or liquid phase.

In a further embodiment, a 3-phase system according to the invention comprises an inner solid phase, which is dispersed in a liquid continuous "outer" phase while surrounded by a gaseous layer.

In yet a further embodiment, a 3-phase system according to the present invention is a system in which the outer phase is solid, wherein there is dispersed a 2-phase system comprising a solid or liquid phase surrounded by a gaseous phase.

Determination if a phase is solid, liquid or gaseous phase is determined at atmospheric pressure and at room temperature, unless otherwise mentioned.

A 3-phase system according to the present invention may require stabilization of one or more of the interfaces separating the phases. This can be achieved by colloidal particles. Colloidal particles according to the invention are solid particles contained in or on the interface. Colloidal particles are defined as usual, i.e. as solid particles with a diameter of 1 nm to 50 m. Furthermore, stabilization may be achieved by other means, in particular by adapting the phases itself rather than by adapting the interface, such as described below.

The size of the second, gaseous phase as expressed in the invention is determined by its diameter, which may be measured by using microscopic images.

The lifetime of a 3-phase system according to the invention is determined by the lifetime of the 2-phase system contained in the outer, third, phase. Generally two ways exist in which this 2-phase system may decay. First, the inner phase may merge with the outer, third, phase. This can occur when the inner and/or the outer phase is liquid. Second, the second, gaseous phase may decay e.g. by dissolution. The lifetime is defined as customary in physics, i.e. the time required for half of the 2-phase system elements to decay. Decay in this respect is more or less exponential, and can be fitted by mathematical methods as is known in the art, to give a time-value for the lifetime. The decay can be monitored by microscopic observation.

A volatile compound, in the context of the present invention, is a compound that is not gaseous, but that is easily converted to the gaseous phase. Often a volatile compound is liquid, and has a relatively low boiling point, and/or a high vapour pressure. Volatile compounds are known in the art, and are usually low-boiling organic liquids. Also, a liquefied gas may be considered a volatile compound.

An inner and/or an outer phase according to the invention may comprise a glass-forming material. A glass-forming material is a material that has a strong tendency to form a glassy state when the liquid in which it is dissolved is cooled or removed. These are generally molecules with a molecular weight sufficiently high to make crystallization difficult. The term "glass" is known in the art, and is defined as an amorphous solid.

Oil/oily refers to the apolar nature of a liquid phase that is organic and therefore displays limited miscibility with water.

The invention discloses a method of producing a 3-phase system comprising an inner, second and outer phase, comprising making a 2-phase system comprising a dispersed and a continuous phase in which the continuous phase is a volatile compound, dispersing said 2-phase system in a third phase to obtain a ternary mixture, and removing or evaporating the volatile compound, so that the second phase becomes gaseous A method for making a 3-phase system according to the invention comprises first making a 2-phase system comprising a dispersed and a continuous phase in which the continuous phase is a volatile compound. This entails making an emulsion in a volatile compound with a non-miscible other phase. Said other, dispersed phase will, after completion of the method, be the inner phase of the 3-phase system according to the invention. It may be solid or liquid, and in case it is liquid, it may comprise additional components, such as fully dissolved solids or fully miscible other liquids. It may also comprise an additional non-miscible phase, such as dispersed solid particles. A liquid inner phase according to the invention may be an organic phase or an aqueous phase.

A volatile compound may be any compound that can easily transform to the gaseous phase under the conditions used. Thus, often such a volatile compound comprises a volatile organic liquid, or a mixture of volatile organic liquids. It is important that the volatile compound is selected such that it is immiscible with both the inner and the outer phase of the 3-phase system. Volatile organic compounds are known in the art, and include for instance, but not exclusively, low-boiling substituted monocarbonic volatile compounds (for instance carbon disulfide, chloroform, dichloromethane), ethers (for instance diethyl ether), esters (for instance methyl acetate, ethyl acetate, propyl acetate), alcohols (for instance pentanol, hexanol), aromatic compounds (for instance benzene, toluene), linear or branched alkanes, fluorocarbons (for instance perfluorohexane) and chlorofluorocarbons (for instance trichlorofluoromethane, dichlorofluoromethane). Preferably in general, substituted monocarbonic volatile compounds, ethers, esters, alcohols or (linear or branched) alkanes are used as a volatile compound, such as for instance carbon disulfide, dichloromethane, chloroform, diethyl ether, methyl acetate, ethyl acetate, propyl acetate, pentanol, hexanol and the linear alkanes pentane, hexane, heptane, octane, nonane and decane and branched analogues thereof. These compounds are preferred as volatile compound because of having a high vapour pressure and a relatively low polarity. Volatile compounds with very low polarity and very high vapour pressure are preferred, such as diethyl ether, carbon disulfide, and the linear alkanes pentane, hexane, heptane, octane, nonane and decane and branched analogues thereof. More preferably alkanes are used, such as pentane, hexane or heptane, most preferably hexane because these have in addition to the above preferred characteristics a boiling point that allows for a practical and safe method.

However, it may be advantageous for certain applications to use a different volatile compound. For instance, when a 3-phase system according to the invention has a pharmaceutical application a volatile compound to be used should result in a pharmaceutically acceptable 3-phase system. This may be achieved by either complete removal of any undesired volatile organic compound, e.g. an alkane, such as hexane, but this may also be achieved by selecting a pharmaceutically acceptable volatile compound from the above-mentioned options.

In another example, a 3-phase system according to the invention is used in food applications. In this case, a volatile compound should be selected such that the resulting 3-phase system results in an acceptable food ingredient. Also here, this may be achieved by either complete removal of any undesired volatile organic compound, e.g. an alkane, such as hexane, but this may also be achieved by selecting a volatile compound that is acceptable in food products from the above-mentioned options.

In a different embodiment, fluidized gas is used as the volatile compound. Advantageously, relatively inert gases are used, so as not to display chemical reactions with the other phases of the 3-phase system during formation. Further advantageously, such gases have a relatively high boiling point, which makes working with a gas as a volatile compound easier and safer. Preferably, gases such as carbon dioxide, nitrogen, hydrogen, or noble gases are used in a method according to the present invention. Most preferably however, carbon dioxide or nitrogen is used because of their wide-spread availability and low price, most preferably carbon dioxide, because it has advantageous interface properties in a method according to the present invention.

Dispersing the first phase into the volatile compound, or of the obtained 2-phase system into the third phase to obtain the ternary mixture, according to the general method of the invention, can be done by any means known in the art to result in an emulsion. Thus, such dispersing can be done by all kinds of known high-shear mixing methods among which shaking, membrane emulsification, homogenization, ultrasound treatment, turrax mixing, microfluidic droplet formation and Phase Inversion Temperature emulsification. Also, mixing of two phases that do not require high shear to result in a 2-phase system characterised as an emulsion may be considered. In such case the emulsion obtained after the first step of the method of the present invention is usually called a micro-emulsion, which can also be used in the present invention.

As a next step, the 2-phase system is dispersed in a third phase, thereby obtaining a ternary mixture. Said third phase is usually liquid at the time of dispersing. Mixing methods comprise but are not limited to all of the above-mentioned methods. The third phase may advantageously be an aqueous or an organic liquid, and it may comprise additional components, such as fully dissolved solids or fully miscible other liquids. It may also comprise an additional non-miscible phase, such as dispersed solid particles. A prerequisite is however that additional components do not interfere with the formation of a 3-phase system in which the outer continuous phase is liquid, and the therein dispersed 2-phase system.

In some cases, the 3-phase system of the invention may be formed in one step, e.g. microfluidic emulsification procedures. Such techniques will be clear and easily performed by the skilled person.

In one embodiment, the outer phase of the ternary mixture is aqueous. In this case, the inner phase may be aqueous or organic, or solid, depending on the application. One embodiment of this type is a 3-phase system in which both the inner and the outer phase are aqueous. This embodiment allows for a wide range of possible applications The ternary mixture obtained in the second step of the present method may for instance be a water-oil-water (wow)-emulsion, in which the organic phase is a volatile compound. In this case, both the outer and the inner phase is an aqueous phase. Also, said ternary mixture may comprise as an outer phase an organic phase that is not miscible with the second phase, i.e. the volatile compound. The phase comprised in the volatile compound in both cases may however alternatively be solid.

A third step in the disclosed method is removing or evaporating the volatile compound. It is important that removing or evaporating the volatile compound is not accompanied by a substantial destruction of the inner and outer phase of the ternary system.

Removing the volatile compound generally means replacing it with a gaseous compound so as to form the gaseous second phase of the 3-phase system of the invention. In one embodiment, the gaseous compound stems from the atmosphere in which the $3^{rd}$ step of the method is performed. As such, it may be any gas or gas mixture in which the method can be performed, and which allows for formation of two interfaces so as to form a 3-phase system. Nitrogen, oxygen, carbon dioxide, fluorocarbons and noble gases, or any mixture thereof, may be used, but preferably, air is used for its availability and compatibility with many applications.

However, in case the inner phase comprises a compound or phase that is susceptible to oxidation, such as a for instance a peptide, a nucleotide or an organic substance such as for instance a pharmaceutical, oxygen is preferably excluded from the atmosphere in which to perform the $3^{rd}$ step of the method of the invention, and which gas eventually replaces the volatile compound. In this case, nitrogen is a preferred gas in which to perform the method and to replace the volatile compound.

Removal of the volatile compound can be achieved by increasing the temperature and/or decreasing the pressure, thereby replacing the volatile compound with a gaseous phase, such as from the atmosphere in which the method is performed. In addition, removing the volatile compound may be achieved by extraction. In this case one may use a second phase that has a low but finite solubility in the third, continuous, phase. The second phase may then be evaporated via the third phase or may be gradually removed by rinsing with fresh continuous phase. The removal of the second phase should be accompanied by the supply of gaseous phase to replace the removed second phase.

Evaporation of the volatile compound usually means that the volatile compound is transformed into the gaseous phase that forms the second phase of a 3-phase system according to the invention. In general, this means that the volatile compound at least partly remains present in the 3-phase system, and is not fully removed. This may conveniently be achieved by using a liquefied gas as a volatile compound. Also, a highly volatile organic liquid may be evaporated to form the gaseous second phase. Evaporating the volatile compound may entail partial removal of the volatile compound, but it is characterised in that at least part of the volatile compound remains present in the 3-phase system as the gaseous layer.

When a fluidised gas is used as the volatile compound, the method of making a 3-phase system according to the present invention is preferably performed at least partly under increased pressure and/or reduced temperature so as to retain to the volatile compound in a liquid state. In such embodiment, removing or evaporating the volatile compound can be done by lowering the pressure and/or increasing the temperature, so as to transform the liquefied gas into its gaseous state. Preferably, reduction of pressure and/or increasing the temperature is done slowly, so as not to apply disrupting forces that prevent formation of a 3-phase system according to the invention.

In a highly preferred embodiment, removing or evaporating the volatile compound is performed by a combination of lowering the pressure and increasing the temperature. An example of this embodiment is a method wherein removing or evaporating the volatile compound is achieved by freeze-drying of the ternary mixture. It is important in this case that the volatile compound can still at least partly escape through the crystallised or glassy outer phase, so as to allow a gaseous second phase to form. This can be achieved by allowing the outer phase to gradually become substantially porous and permeable to the volatile compound. Thus, the porosity allows for gas to replace the volatile compound when freeze-drying is stopped and the pressure is increased.

As an alternative, it is possible to select a combination of volatile compound and outer phase in which the volatile compound dissolves to some extent in the (solidified) outer phase such that the volatile compound during its removal can permeate through the outer phase.

Freeze-drying has the advantage that the low temperature may cool any phase to such an extent that it solidifies, e.g. by freezing. A solidified phase generally has increased strength to a non-solid phase, and as such may have higher resistance to the stress that is brought into the system by evaporating or removing the volatile compound. This stabilises the 3-phase system of the invention during formation.

At the same time, the low pressure, such as for instance a vacuum, allows easy transformation of the volatile compound into the gas phase, which may bring along easier removal. In case the volatile compound is fully removed, repressurising the chamber in which the $3^{rd}$ step of the method is performed allows a gaseous phase to enter the system, thereby replacing the volatile compound and forming a 3-phase system according to the invention.

When freeze-drying is performed not at vacuum, but at reduced pressure, the volatile compound may also be evaporated. In this case, repressurising the chamber allows a gaseous phase to enter and at least partially supplement the gaseous phase present. It may not be necessary to stabilise the inner and/or the outer phase by freezing during evaporation of the volatile compound. This may be a preferred method in case a 3-phase system according to the invention of relatively large size is required.

In case the outer phase is liquid and the volatile compound is replaced with a gaseous phase, it is important that the gaseous phase replacing the volatile compound is supplied at a rate that more or less matches the rate at which the volatile compound is removed. If these rates do not match the 2-phase system contained in the third, continuous, phase will either shrink or expand which may damage the 3-phase system. When freeze-drying is applied the volatile compound is first removed and only at the end of the process the gas is supplied during repressurising. However, since the third phase is solid, it can withstand the stresses developing during this process.

3-phase systems in which the second phase is gaseous have generally been found to display a low stability and short lifetime. For this reason, stabilisation of the 3-phase system of the invention is preferred. Stabilisation can be achieved by adsorption of surface active particles or molecules, preferably surface active particles, on the interface that separates 2 phases of the ternary mixture, and retaining them on the interface during removal or evaporating of the volatile compound. This stabilises said interface of the 3-phase system of the invention. Such stabilisation has the advantage that the interface between the outer phase and second (gaseous) phase, and/or the interface between the second (gaseous) phase and the inner phase contained therein, remains stable for a prolonged time. Stabilisation in this respect also means that the 3-phase system has an increased lifetime as compared to a 3-phase system of equal constitution but not having been stabilised.

Preferably, the surface active particles or molecules comprise colloidal particles. The adsorption of colloidal particles at the interface usually results in an interface that behaves as a solid. An interface coated with colloidal particles will not likely merge with another colloidal particle-coated interface even when this is thermodynamically more favourable. A colloidal particle-coated interface will also strongly resist compression. On the other hand, a phase coated at its interface with adsorbed colloidal particles can still be deformed or made to expand. Colloidal particle adsorption thus retains several of the useful properties of droplets and bubbles. This makes colloidal particle-adsorption a very advantageous way of stabilizing a 3-phase system according to the invention.

Colloidal particles in the present invention are particles ranging in size from about 1 nm to about 50 micron. Preferably we use colloidal particles in the size range of 5 nm to 5 m, more preferably 10 nm to 1 m, even more preferably 50 nm to 500 nm. The particles are preferably at least partly hydrophobic in order to adsorb to an interface of the 3-phase system.

Examples of suitable particles are: hydrophobised silica, mineral particles, fat particles, wax particles, fatty acid particles, surfactant particles such as mono- and diglycerides particles, particles consisting of esters of fatty acids and polymer particles where the polymers may be cellulose or cellulose derivatives, polystyrene, poly-lactic acids, polyglycolide, poly-lactide, proteins, starch and starch derivatives, proteins, chitin and chitin derivatives, acrylic polymers and so-called enteric polymers such as Eudragit (which is an acrylic polymer). Using hydrophobised fumed silica particles it was possible to produce 3-phase systems in the micron range with both the core phase and the continuous phase being aqueous (i.e. so-called antibubbles) with a lifetime in the order of at least several hours when we used HDK H18 particles and HDK H30 particles (supplied by Wacker chemie) to stabilise the inner and outer interface respectively. A lifetime of about 10 minutes was found when HDK H30 particles and R816 particles (supplied by Evonik) were used at the inner and outer interface respectively. The contact angle of the particles at the oil-water interface $\theta_{ow}$ as defined in Langmuir 2002, 18, 1270-1273) is the most determining factor for how well particles will stabilise a polar/apolar interface. For dodecane-water this contact angle is 80° for the HDK H30 particles and is estimated to be 65° for the R816 (see Langmuir 2002, 18, 1270-1273). We thus expect that in these circumstances in order to obtain a lifetime of 10 minutes or more at the inner interface particles with an oil-water contact angle of at least 80° and at the outer interface particles with an oil-water contact angle of at least 65° need to be used. The skilled person can easily choose the appropriate particles on basis of these observations. In other circumstances, the skilled person can easily determine the optimal particle constitution and size.

Particles may however also be hydrophilic, and in that case are preferably hydrophobised in situ by the adsorption of surfactants. An example of this is the combination of hydrophilic positively charged calcium carbonate particles hydrophobised by the adsorption of negatively charged SDS surfactant.

Particles may also be used that are hydrophobic but due to e.g. the presence of some ionisable groups at their surface still are water-dispersible (see e.g. Langmuir 2006, 22, 4968-4977). Or, particles may be hydrophilic but they may be hydrophobised by adding an additive that adsorbs to the particles to make them hydrophilic. Alternatively, the particles may be hydrophobic but their dispersal in the hydrophilic phase is facilitated by an additive added to the aqueous phase. In these cases, it might be possible to produce a 3-phase system according to the invention with an aqueous outer phase and an aqueous inner phase directly without the use of the intermediate step of first producing a double emulsion. This then can be done for example using microfluidic methods in which a concentric flow of the first phase (containing the stabilising particles) and of the second gaseous phase is simultaneously dispersed in the third, continuous, phase. If an additive is used to help hydrophobic particles disperse in the aqueous phase or phases, this additive may subsequently be removed to stimulate the particles to adsorb at the interfaces or interfaces.

For several applications it will be advantageous when the properties of the particles are variable with respect to environmental properties such as pH and temperature. If the particles stabilising the interface(s) of the 3-phase system of the invention respond to changes in the environment the 3-phase system may release the contents of the core phase in response to environmental triggers. Examples of such particles are particles that dissolve in a certain pH range such as certain mineral particles (for instance calcium carbonate), fatty acids, salts of fatty acids with multivalent cations and particles produced from enteric polymers such as Eudragit. Also, examples exist of particles that vary in their wettability in response to pH changes, such as oleic acid coated $Fe_3O_4$ particles, hydrophobised fumed silica particles or SDS coated calcium carbonate particles.

Generally, colloidal particles that are predominantly wetted by the organic phase will be used to stabilize the interface of an aqueous phase inside an organic phase. Conversely, colloidal particles that are predominantly wetted by the aqueous phase will be used to stabilize the interface of an organic phase inside an aqueous phase.

Solid-like interfaces, including interfaces having absorbed colloidal particles, and also including interfaces with absorbed other solids, should not be considered an additional phase of the 3-phase system of the invention.

Adsorption of surface active particles or molecules, such as colloidal particles, for stabilisation of an aqueous phase inside an organic phase may be achieved by dispersing the particles or molecules in the organic phase and then dispersing the aqueous phase to be stabilised. The particles/molecules will then be driven to the interface because of thermodynamics. When an organic phase inside an aqueous phase needs to be stabilised the particles/molecules are first dispersed/dissolved in the aqueous phase and subsequently the organic phase is dispersed. The amount of particles/molecules should be at least sufficient to provide monolayer coverage of the interfacial area. Generally at least about two times the minimal required amount of surface-active material is used to allow fast coverage of newly formed interfaces during the dispersal of the two phases. The right amount of surface-active material to be used can be easily determined by a person skilled in the art. In some cases however a polar phase may be stabilised inside an apolar phase by particles that are first dispersed in the polar phase, for example when the hydrophobicity of these particles is increased by adsorption of an additive such as a surfactant or when dispersion of hydrophobic particles in the polar phase is facilitated by the presence of a temporarily present additive. Likewise, one could stabilise an apolar phase inside a polar with the help of particles first dispersed in the apolar phase.

Another means of stabilising the 3-phase system of the invention is by increasing the stability of the outer phase and/or the inner phase of the ternary system before or during removing or evaporating the volatile compound. Such methods will be called phase stabilisation. This could be done by various methods, including, but not limited to, gelling/vitrification, cooling, drying and/or crosslinking the outer phase and/or the inner phase of the ternary mixture to allow removal of the volatile compound and/or stabilise the 3-phase system of the invention in which the second phase is gaseous.

In one preferred mode of the invention, any aqueous phase present additionally comprises a glass-forming material. This should be interpreted to mean that if only one aqueous phase is present, this phase may comprise a glass-forming material. In case two aqueous phases are present, either one or both of these may comprise a glass-forming material.

A glass-forming material can be any compound that by adaptation of the conditions becomes a glass. Generally, adaptation of conditions to form a glass requires cooling and/or lowering the percentage of solvent. Thus, by including a glass-forming material in any aqueous phase, it gains strength and thus stability, and therefore aids in maintaining a ternary system during removing or evaporating the volatile compound. This process is known as vitrification in case the liquid phase forms a highly viscous, near-solid, glass-like state. It is known as gelling in case a highly viscous state of lesser viscosity than a glass results. Both cases are highly preferred in a method according to the invention.

Glass-forming materials that are capable of forming a glass in an aqueous phase during removing or evaporating of the volatile compound can be selected based on the temperature range at which vitrification or gelling is required. Suitable glass-forming materials can be (bio)polymers, artificial or natural peptides and proteins, carbohydrates, polysaccharides, or metals. Preferably, carbohydrates are used, such as dextrin, preferably maltodextrin. An overview of glass transition temperatures and how these depend on the presence of solvents can be found in several text books, such as, for biopolymers, 'Physical Chemistry of Foods' by P. Walstra.

Alternatively, a liquid organic phase may be subjected to solidification. This can be achieved by vitrification. For instance, a glass forming material may be added to vitrify an organic phase. This can be any solid that dissolves in the organic phase as long as the molecular weight of the substance and its concentration is such that a glass transition temperature in a practical range is obtained. Examples are polyacrylates, polystyrene, and polycarbonates and copolymers of vinyl chloride with methyl methacrylate. Alternatively, so-called "organic glasses" may be used, which comprise organic liquids that by cooling to a given temperature range form a glass with a temperature-dependent viscosity. Examples of such organic glasses are a combination of methylcyclohexane and methylcyclopentane in a volume ratio of 1:1, or a combination of isopentane with methylcyclohexane in a volume ratio of 3:1. Secondly, cooling may stabilise a phase while removing or evaporating the volatile compound by freezing it, thereby converting it to a solid state, which enhances strength. Cooling may include glass-formation as discussed above, and it may also involve crystallisation. In a preferred embodiment, after cooling the ternary mixture and subsequent removal or evaporation of the volatile compound, the remaining 3-phase system of which the second phase is now gaseous, is stable also after thawing the inner and/or the outer phase.

In a highly preferred embodiment, cooling as described above is followed by a reduction of pressure. An example of this embodiment is freeze-drying, as discussed above. In this embodiment, cooling stabilises the outer and/or the inner phase via crystallization and/or vitrification, e.g. the formation of a glassy state. The accompanying decrease in pressure induces removal or evaporation of the volatile compound.

Drying can be used as well to stabilise a remaining phase so as to allow removal of the volatile compound. Drying is usually performed in combination with dissolved solids, so that removal of the liquid phase in which these solids are dissolved by drying results in a remaining solid state. Dissolved solids in this respect may advantageously be dissolved natural or artificial polymers, salts, carbohydrates, sugars. Preferably, carbohydrates such as maltodextrin are used.

A fourth option to stabilise a phase is by crosslinking. Two options exist: either a crosslinkable solid is used to create a so-called polymer gel, or use is made of a liquid phase which is itself polymerisable.

Dissolved crosslinkable solids may include polyvinylalcohol (PVA), polyacrylicacid (PAA) and polyacrylonitrile (PAN), proteins. Crosslinks need not necessarily be covalent but can also be ionic, hydrogen bonds, or other types of molecular interaction. Examples of solids that form these kinds of gels are cellulose derivatives, (hydrophobised) clay, charged polysaccharides such as alginate and pectin, proteins, certain emulsifiers such as sorbitan monostearate. Gelled organic phases are generally referred to as organogels or oleogels and a wide range of literature exists covering those.

A liquid phase which is itself polymerisable is usually an organic liquid, comprising polymerisable organic monomers. A phase comprising polymerisable organic monomers may be polymerised, for instance by addition of a suitable initiator such as a peroxide, an acid or a base. Also, light may be used to induce polymerisation of such phase. A method including this option is therefore a method in which the outer phase is subsequently polymerised.

This option results in the outer phase of the 3-phase system being a solid, i.e. a polymer, in which a gaseous second phase is comprised, that in turn comprises a third phase that may be solid or liquid. This option is preferred for making foamed materials with special properties. Monomers that allow polymerisation induced by any of the above means are known in the art, and include but are not limited to polystyrene, polyurethane, polyacryl-, polyvinyl-, polyolefin-, and polyester polymers, and copolymers thereof. Preferably, polystyrene or polyurethane are used.

Combinations of the above methods of stabilising a liquid phase may be readily conceived by the skilled person, and are considered to be included in the method of the invention. The combination of phase stabilisation with removal of the organic compound was already mentioned under freeze-drying. Also, a highly preferred embodiment is the inclusion of a glass-forming material in an aqueous phase while adsorbing colloidal particles onto at least one interface layer. An example of such an embodiment is a 3-phase system that includes stabilisation of one or more of the interfaces by hydrophobised fumed silica, and stabilisation of at least one aqueous phase by inclusion of the glass-forming material maltodextrin in all of the aqueous phases present. In a different embodiment, colloidal particles are used in combination with organic glasses or gelled organic liquids, to obtain a 3-phase system in which the middle phase is air and the inner and/or outer phase is organic.

Furthermore, a 3-phase system may be prepared by stabilising the interface layers of a 2-phase system with colloidal particles in a dispersion in an organic monomer, which may subsequently be polymerised. It is much preferred to use colloidal particles on all interfaces, in combination with any of the phase stabilisation methods gelling/vitrification, cooling, drying and crosslinking. In these embodiments, colloidal particles stabilise the 3-phase system of the invention during and after formation, whereas phase stabilisation ensures that stresses during removal of the volatile compound do not disrupt the 3-phase system during formation. Thus, colloidal particles can also be used in combination with drying, and also in combination with cooling (i.e. freezing).

The 3-phase systems obtained with the method of the invention are characterised in that they have a lifetime of at least 3 minutes. However, lifetimes of much longer than 3 minutes can be achieved, such as for instance a lifetime of at least an hour, or of at least a day. Also, lifetimes of at least one week, or even at least on month can be achieved, depending on the constituents of the three phases and stabilisation strategies that have been applied.

In addition, 3-phase systems obtained by a method of the invention can be obtained having a size of the second, gaseous phase dispersed in the outer phase that allows for various applications. For instance, 3-phase systems wherein the diameter of the second phase has a size smaller than 1 mm have been obtained with a method of the present invention. Preferably, the size obtained is between 100 nm and 1 mm, more preferably between 0.1 m and 100 m. This allows for many food-and/or pharmaceutical applications.

Any combination of the above ranges of lifetime and diameter of the second, gaseous phase can be obtained with a method according to the invention by suitable adaptation of the various methods of stabilisation of the interfaces and/or of the inner and outer phase during or after removal of the volatile compound. In a most preferred embodiment however, a 3-phase system obtained with a method according to the invention comprises a dispersed gaseous phase comprising at least one other phase, which dispersed gaseous phase has a diameter smaller than 1 mm and has a lifetime of at least 3 minutes. This may most advantageously be achieved as mentioned herein, i.e. with a 3-phase system that includes stabilisation of one or more of the interfaces by hydrophobic particles, such as fumed silica, and stabilisation of at least one aqueous phase by inclusion of the glass-forming material maltodextrin in all of the aqueous phases present.

The invention equally pertains to a 3-phase system that can be obtained with the above method. Thus, the invention comprises a 3-phase system comprising at least an inner, second and outer phase wherein the second phase is gaseous, comprises at least an inner phase and is dispersed in the outer phase, said 3-phase system having a lifetime of at least 3 min and wherein said second phase has a diameter of less than 1 mm.

The 3-phase system can consist of droplets of a liquid inner phase inside a gaseous second phase inside a liquid, continuous outer phase. The liquids can comprise a polar liquid (such as an aqueous solution) or an organic liquid. The inner and outer phase may also further comprise one or more additional phase(s), as in themselves being an emulsion or dispersion.

A 3-phase system of the invention in which the outer phase is solid may be an alternative to e.g. currently used foamed metals and polymers. The presence of a phase inside the bubbles may modify the rheological/mechanical properties of the material. In addition, presence of this phase will increase the weight of bubbles which may lead to a more homogeneous material.

One specific embodiment of such a 3-phase system is a system in which both the inner and the outer phase are liquid. In such case, a 3-phase system according to the invention is a solution comprising an antibubble. Thus, an antibubble is a special case of a 3-phase system according to the invention. Antibubbles according to the invention have a lifetime of at least 3 minutes and a diameter smaller than 1 mm. The inner phase of such an antibubble may be aqueous or organic, and may additionally comprise dispersed or dissolved solids, such as salts, glass-forming materials, pharmaceutical compounds, nucleotides or peptides. Preferably however, in case the antibubble is used for delivery of releasable compounds, the inner phase of the antibubble is not gelled. Also, solids may be included in the inner phase of an antibubble according to the invention so that the density of the antibubble is altered relative to the density of the surrounding outer phase. This results in sinking, floating or neutral buoyancy bubbles. Any antibubble solution is most preferably obtained by freeze-drying of a ternary system comprising three liquid phases, of which the second phase is a volatile compound. Thus, the invention equally pertains to a freeze-dried powder that upon reconstitution with a liquid provides an antibubble solution.

For many applications, an aqueous outer phase is preferred. Further preferably, the outer phase comprises a water-soluble solid, such as a salt or a glass-forming material.

In another embodiment, the inner phase is aqueous. Preferably, such aqueous inner phase comprises a water-soluble compound. Much preferred however is a 3-phase system comprising an inner phase, wherein both the inner and the outer phase are aqueous. Most preferably in this embodiment, the outer aqueous phase comprises a water soluble solid such as a glass-forming solid as defined above, and/or the inner aqueous phase comprises a water-soluble compound, such as a pharmaceutical compound, food compound, or any compound or even biological entity (such as a virus, nucleotide, peptide, cell, etc.) that needs to be encapsulated and/or delivered) or any combination thereof. In all cases, the inner phase may additionally comprise a dispersed solid or liquid, which for the context of the present invention is still considered a 3-phase system.

In all of the above embodiments, a 3-phase system of the invention can be used as a pharmaceutical carrier, by encapsulating a pharmaceutically active compound. Envisioned compounds are all kinds of drugs but also potentially biological material, such as viruses, nucleic acids, peptides, proteins and cells. When such use is envisioned, care has to be taken that all constituents are pharmaceutically tolerated. In particular when the 3-phase system will be applied inside the blood stream, the materials forming the 3-phase system should be chosen to be compatible therewith. In such a case the glass forming solids present in both aqueous phases could for example be selected from the group of substances present already in blood, such as glucose, amino acids and/or blood derived proteins, or substances that are frequently used intravenously such as hydroxyethyl starch or dextran. Also stabilising colloidal particles should be chosen from the group of materials already present in blood or frequently used in blood. One could thus use particles made of amino acids, fatty acids, phospholipids or particles made of pharmaceutical polymers such as (co)polymers of lactic acid and glycolic acid.

It is further possible to take care that all constituents of the 3-phase systems are acceptable food ingredients. This has the advantage that such a 3-phase system can be used in a food product, or as a pharmaceutical carrier that is to be ingested. This may be achieved by using as glass forming solids carbohydrates, proteins and combinations thereof and as stabilising colloidal particles consisting of fats, fatty acids, salts of fatty acids, emulsifiers, minerals, protein, cellulose and derivatives thereof.

It is also possible that the inner phase comprises a solid. This way, solid particles may be encapsulated. Especially, such particles may be heavy, altering the density of the dispersed second phase comprising the solid inner phase. This may allow a 3-phase system according to the invention to be used to create sinking, floating, or neutral buoyancy bubbles. This is especially favourable in combination with use as a food product as described above. Examples of use of such sinking bubbles include bubbles containing one or more hydrophobic starch particles, hydrophobic amino acid particles, hydrophobic protein particles or ethylcellulose particles. Sinking, floating or neutral buoyancy bubbles can also be obtained using a liquid inner phase. For example, a 50% solution of maltodextrin 33DE has a density of around 1.3 g/ml. A 10 micron bubble containing a 50% maltodextrin solution core with a size of 9.2 micron or more would thus sink. Non-creaming bubbles constituting a foam would be advantageous for example because this foam will have a longer lifetime. Also, in some products it will be advantageous to add bubbles that remain dispersed throughout the product instead of forming a foam layer. Other food applications of the 3-phase systems of the invention are the encapsulation of substances such as minerals, vitamins, probiotic cells and flavours.

In a different embodiment, the inner phase may comprise an organic liquid. This may be suitable in case an application requires encapsulation of a hydrophobic particle or an apolar solute by a 3-phase system of the invention. Examples of this embodiment are the encapsulation of apolar drugs.

Another embodiment makes use of a continuous outer phase that is an organic liquid. In this case, in one of the preferred embodiments the organic liquid is polymerisable as described above. In that case, the method of the invention includes an additional step of polymerising the outer organic liquid so as to form a solid phase, that comprises a dispersed gaseous phase comprising at least one other phase. A 3-phase system obtained by such method is considered included in the invention, and may be used in various applications such as foamed polymers. Foamed polymers already find numerous applications. Use of this invention to produce foamed polymers in which the bubbles contain an inner phase may lead to more advantageous mechanical properties.

In the remaining part, focus will be on specific embodiments, and their specific methods of preparation and use.

Antibubbles can be produced as follows. First, a 2-phase system comprising an inner organic or aqueous phase in a volatile compound is created. Dispersion of the inner phase in the volatile compound can be done by all kinds of known dispersion methods such as shaking, membrane emulsification, homogenization, ultrasound treatment, microfluidic droplet formation, turrax mixing or Phase Inversion Temperature emulsification. A microemulsion may also be used.

The obtained 2-phase system is dispersed in a third phase to obtain a ternary mixture using any of the above mentioned techniques of making a dispersion. Finally, the volatile compound will be either removed and replaced by a gaseous phase or will be evaporated into a gaseous phase that at least partly remains present as the gaseous phase of the antibubble. It is important that removal of the volatile compound is not accompanied by very substantial removal of the inner and outer phase. In general, ways to remove the volatile compound may be evaporation by either increasing the temperature and/or lowering the pressure, or extraction. It is advantageous when during removal of the volatile compound the inner and/or the outer phase of the system are solid such that stresses that develop during removal of the volatile compound do not destroy the structure of the 3-phase system. This can be done by (reversible) gelling, crosslinking, drying or cooling.

We will now describe in more detail a particular way of producing antibubbles in which the first and third phase are aqueous.

An aqueous solution is emulsified in volatile compound. Preferably the volatile compound contains dispersed colloidal particles with hydrophobicity sufficient to make the particles adsorb at the oil-water interface. Examples are hydrophobised silica particles, polystyrene particles, ethylcellulose particle, fat or surfactant particles, (coated) mineral particles, particles made of Poly-DL-lactic acid and poly (DL-lactic-co-glycolic acid). Preferably the particles are wetted better by the volatile compound than by the aqueous phase. We have found that particles with a dodecane-water contact angle greater than 80° are particularly advantageous. The inner phase has as a continuous phase an aqueous phase but may also contain an additional phase such as droplets or particles. The inner phase may preferably comprise an active compound that is to be encapsulated in an antibubble. Such an active compound may for instance be a pharmaceutical compound, a virus, a nucleotide, a peptide, a mineral, a vitamin, a cell or a flavour. The inner phase preferably further comprises a glass-forming material.

The thus prepared 2-phase system is subsequently emulsified in a third, outer, aqueous phase. This phase preferably comprises a glass forming material. This phase preferably also contains dispersed colloidal particles with a hydrophobicity sufficient to make the particles adsorb at the oil-water interface. Preferably the particles are wetted better by the aqueous phase than by the volatile compound. We have found that particles with a dodecane-water contact angle greater than 65° are particularly advantageous. Subsequently the volatile compound is removed or evaporated by any of the means described above, e.g. by increasing the temperature and/or decreasing the pressure. Preferably these approaches are combined, such as in freeze-drying.

When freeze-drying is ready the vacuum is removed by the addition of gas. In this step a gas can be chosen to replace or supplement the removed or evaporated volatile compound. Freeze-drying produces a powder in the form of a glassy matrix containing gas bubbles that contain one or more particles of the dried or solidified inner phase. When reconstituting this powder in water both the inner and the outer phase will take up water, and a dispersion of antibubbles is produced.

We found that it is particularly advantageous to use colloidal particles to stabilize a 3-phase system in the form of an antibubble.

A solution comprising antibubbles in which the inner phase is either organic or aqueous and the outer phase is organic may be polymerized in case the outer phase comprises a polymerisable organic compound. This results in a stable antibubble-containing solid.

In addition to the uses mentioned above, antibubbles may also be used for controlled mixing of (reactive) substances. This is particularly advantageous when fluids needs to be dosed at locations that are difficult to reach. It may also be advantageous when a sudden mixing of fluids is required, e.g. in case of a precipitation reaction or when a homogeneous and/or fast reaction is required. In these cases the antibubbles encapsulating at least one of the reactive substances can be mixed with the second fluid. The encapsulated substance can subsequently be released almost instantaneously and homogenously by applying e.g. a pressure pulse that makes the antibubbles burst.

In food applications the antibubble systems of the present invention can advantageously be used in dairy products, such as yoghurts and puddings, or in candy, where the antibubbles can give a surprising mouth feel effect. In such an application it can be envisioned that the antibubbles contain colorants that change color upon release, thereby creating a special effect in the food.

In another embodiment, it can be envisioned that antibubbles that are made of temperature-sensitive compounds contain marker substances that are freed when the antibubble system has been subject to (too) high temperatures. In such a way it is possible to inherently use the antibubbles as a warning system for heat exposure.

Additionally, encapsulation applications of antibubbles will not be limited to food and drug delivery but can be applied in any other technological field.

Further use of antibubbles may be as lubricants, since an antibubble dispersion will have rheological properties different from that of dispersions of ordinary bubbles. Furthermore, it is envisaged that antibubbles can also be used in reaction engineering, e.g. in multiphase reactions. An example could be a three phase reaction involving 2 fluids and a gas in which the two fluids should be prevented from reacting directly with each other. An example could also be a gas-liquid reaction in which the liquid core just serves to slow down rising of the bubbles and thus to increase contact time between the gas and the outer liquid.

In another embodiment, the core of the antibubble can be used to transport gasses, e.g. when the core comprises a haemoglobin or a bicarbonate solution, for use in bioreactors.

Other uses of antibubbles are use as filter media. Generally speaking, antibubbles may find application in all technological fields where use is already made of bubbles and/or foaming/foams.

The invention will further be illustrated by the following specific examples.

EXAMPLES

Example 1

Figure 2:
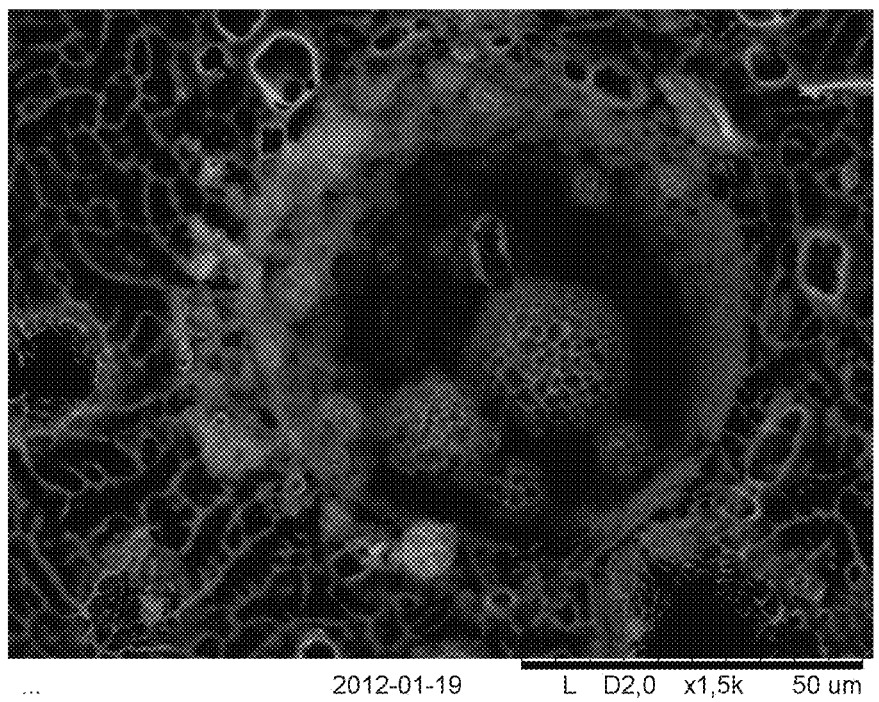
FIG. 2. Scanning Electron Microscopy picture of the freeze-dried emulsion that forms a stable 3-phase system of which the inner and outer phase are liquid and the middle phase is gaseous, i.e. an antibubble dispersion, after reconstitution.
Figure 3A:
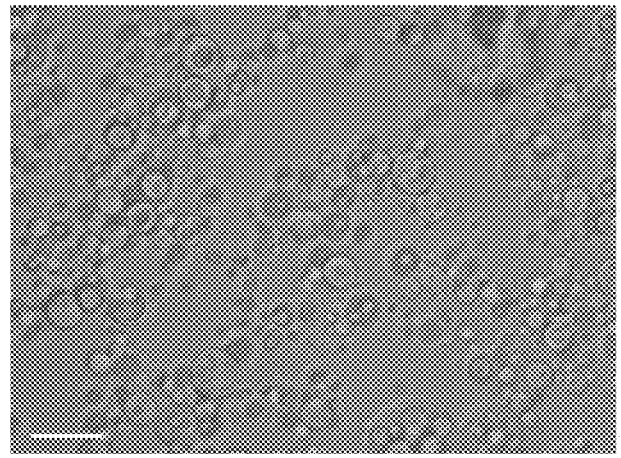
FIG. 3. Top picture: microscopic image of antibubble suspension with arrows indicating some examples of cores inside bubbles. Scale bar=50 micron. Inset: antibubble at greater magnification. Scale bar=25 micron. Below: double emulsion from which the antibubble suspension was produced. Scale bar=25 micron.
Figure 3B:
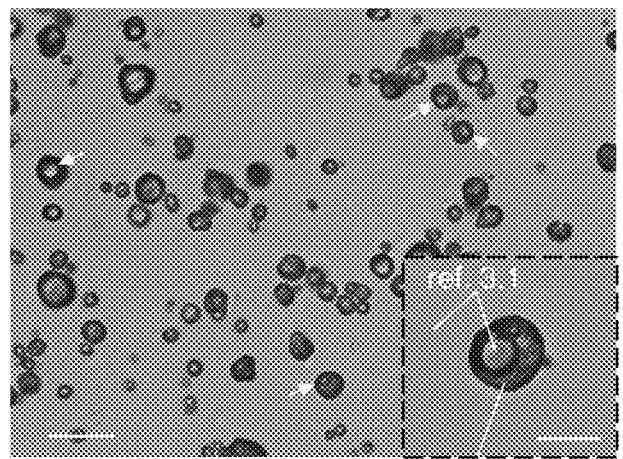
Figure 4:
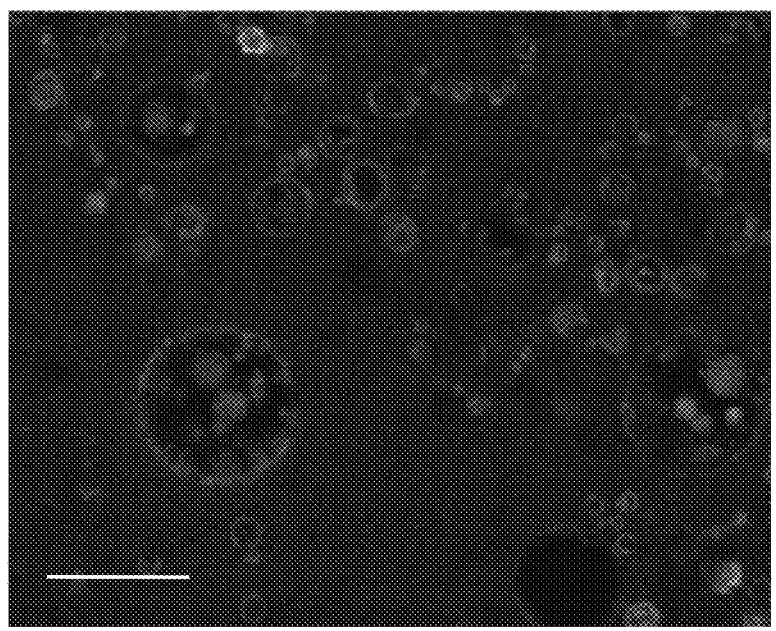
FIG. 4. Confocal Scanning Laser Microscopy image of an antibubble dispersion. Green=FITC (fluorescein isothiocyanate), purple=Rhodamine B. Scale bar=50 micron.

Antibubbles were produced in the following way. A 25% maltodextrin 33DE (Roquette) solution was emulsified at a concentration of 30% in hexane containing 2.5% of hydrophobised fumed silica particles. Emulsification was done using a turrax mixer (IKA werke) at 20,000 rpm. The resulting water-in-oil emulsion was emulsified at a concentration of 25% in water containing 25% maltodextrin of 33 DE (dextrose-equivalents) and 0.5% hydrophobised fumed silica to create a particle-stabilised water-in-oil-in-water emulsion. Emulsification was done using the same turrax mixer at 10,000 rpm. The fumed silica particles stabilizing the water droplets were type HDK H18 and the particles stabilizing the oil droplets were type HDK H30 (both types supplied by Wacker Chemie). The hydrophobicity of the particles may be characterized by their carbon contents. These were 4.5% for the HDK H18 (most hydrophobic) and 2% for the HDK H30. Fumed silica particles were dispersed in the hexane or water phase using an ultrasound probe. Dispersed particles have an average size well below 1 µm. Water-in-oil-in-water emulsions were quickly frozen by contacting a 100 ml glass beaker containing 10 gram of emulsion with liquid nitrogen. The frozen w/o/w emulsion was subsequently freeze-dried for 20 hours (during which the pressure dropped from 80 Pa to 40 Pa) using a Virtis freezemobile 25XL freeze-dryer. Freeze-drying removed both the water and the hexane from the w/o/w emulsion. A SEM picture of the fractured dried material can be found in FIG. 2. If the dried material is dissolved in water the dried w/o/w droplets form bubbles containing droplets of aqueous solution, i.e. antibubbles are formed (FIG. 3*b*). A comparison of FIGS. 3*a* and 3*b* shows that the antibubbles are a good reproduction of the w/o/w emulsion used as a template but then with the oil phase removed and replaced by gas. FIG. 4 shows a cslm image of an antibubble dispersion in which the cores were labelled using a fluorescent dye (FITC). A dye that is soluble in water but is rather hydrophobic (Rhodamine B) was added to the continuous phase of the antibubble dispersion. The fact that this dye does not colour the shell and the core of the antibubbles shows that the hexane is removed from the shell during freeze-drying and that the resulting gaseous shell is a good barrier. It can be seen from FIG. 4 that the dispersion contains bubbles as small as 10 micron, and possibly smaller, that contain a core. FIGS. 3 and 4 show that next to antibubbles the dispersion also contains some bubbles without a core, i.e. ordinary bubbles. The described method can thus also be used to make stable microbubbles. The stability of the antibubbles was checked in two ways. First the antibubble dispersion was kept in a closed beaker for three days and then observed microscopically. The antibubble dispersion still showed a large quantity of antibubbles. Second, a small quantity of antibubble dispersion was put on an object glass, covered with a cover glass and the edges were sealed to prevent evaporation. The sample was imaged at the same position fresh and after one hour showing that none of the antibubbles has lost their core. Since the antibubbles had sizes of 10 micron or more they showed little Brownian motion. Also, their low density led to the bubbles being pushed to the bottom of the cover glass. In addition, since the volume of antibubble dispersion was sealed, no flow was present. These effects combined caused the antibubbles to be still at about the same position after one hour such that we could easily assess if they were still intact. For e.g. smaller antibubbles one could make use of a cell counting chamber, such as supplied by Bürker, to assess the lifetime or monitor the release of a tracer compound added to the inner phase.

Example 2

Example 1 was repeated while using HDK30 particles to stabilize the inner interface and using Aerosil R816 (Evonik) silica particles to stabilize the outer interface. The order of hydrophobicity is H18>H30>R816. For thus produced antibubbles it generally took around 5-10 minutes for the core to escape from the bubbles, i.e. the antibubbles had a lifetime of around 5-10 minutes, as observed microscopically. This example shows that the stability of the antibubbles, and hence their sensitivity to release triggers, can be tuned.

Reference List to FIGS. 1-3-5a-5b

Figure 5A:
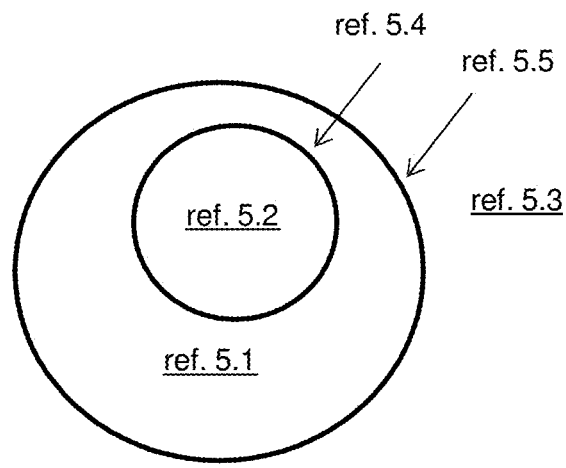
FIG. 5a. Example of a 3-phase system. The entity denoted by phase 1 can be solid or liquid. The liquid may be apolar, polar, an emulsion or a dispersion. Similarly the surrounding liquid may be polar or apolar and solid or liquid. The gas phase may also contain more than 1 entity phase 1.
Figure 5B:
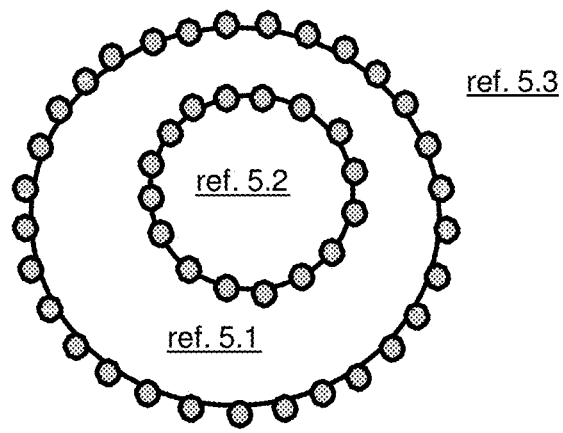
FIG. 5b. Example of a 3-phase system. The entity denoted by phase 1 can be solid or liquid. The liquid may be apolar, polar, an emulsion or a dispersion. Similarly the surrounding liquid may be polar or apolar and solid or liquid. The gas phase may also contain more than 1 entity phase 1. One or both (shown here) interfaces can be stabilized by adsorbed particles, such as colloidal particles.

FIG. 1—ref. 1.1=Microbubble
—ref. 1.2=Inside microbubble shell
—ref. 1.3=Outside microbubble shell
—ref. 1.4=Drug dissolved in oil layer inside the shell
—ref. 1.5=Incorporation of drugs in the shell
—ref. 1.6=Drug
—ref. 1.7=Electrostatic binding to the shell
—ref. 1.8=Attachment of nanoparticles with avidin biotin linkage
FIG.—ref. 3.1=Aqueous phase
—ref. 3.2=Air
FIG. 5a-5b—ref. 5.1=Gas
—ref. 5.2=Phase 1
—ref. 5.3=Phase 3
—ref. 5.4=Inner interface
—ref. 5.5=Outer interface

I claim:

1. A 3-phase system comprising at least an inner, second, and outer phase, wherein the inner phase is liquid or solid, the second phase is gaseous, and the outer phase is liquid; the inner phase is dispersed in the outer phase; the second phase has a diameter of less than 1 mm; and the 3-phase system is stabilized by surface-active colloidal particles and has a lifetime of at least 3 min.

2. The 3-phase system according to claim 1, wherein the outer phase is aqueous.

3. The 3-phase system according to claim 1, wherein the inner phase is aqueous.

4. The 3-phase system according to claim 1, wherein the inner phase comprises a pharmaceutical compound or food compound.

5. The 3-phase system according to claim 1, wherein the inner and outer phases consist of acceptable food ingredients.

6. The 3-phase system according to claim 1, wherein the second phase has a diameter of less than 100 microns.

7. The 3-phase system according to claim 1, wherein the outer phase comprises an organic liquid.

8. The 3-phase system according to claim 7, wherein the organic liquid comprises a polymerisable organic liquid.

9. A 3-phase system obtainable by polymerising a 3-phase system according to claim 7.

* * * * *